United States Patent [19]
Wilsey et al.

[11] Patent Number: 5,707,820
[45] Date of Patent: Jan. 13, 1998

[54] REAGENT AND ASSAY METHODS INCLUDING A PHENAZINE-CONTAINING INDICATOR

[75] Inventors: Christopher D. Wilsey, Carmel, Ind.; Helmut Freitag, Weinheim, Germany

[73] Assignee: Boehringer Mannheim Corporation, Indianapolis, Ind.

[21] Appl. No.: 598,181

[22] Filed: Feb. 7, 1996

Related U.S. Application Data

[63] Continuation of Ser. No. 150,751, Nov. 12, 1993, abandoned, which is a continuation-in-part of Ser. No. 762,278, Sep. 19, 1991, abandoned.

[51] Int. Cl.$^6$ .............................. C12Q 1/54; C12Q 1/26; C12Q 1/28; C07D 241/46
[52] U.S. Cl. .............................. 435/14; 435/25; 435/26; 435/28; 435/15; 435/18; 435/20; 435/7.91; 436/63; 544/347
[58] Field of Search .............................. 435/14, 25, 26, 435/28, 15, 18, 20, 7.91; 544/347; 436/63

[56] References Cited

U.S. PATENT DOCUMENTS

| | | | |
|---|---|---|---|
| 3,791,988 | 2/1974 | Josef et al. | 435/26 |
| 3,891,507 | 6/1975 | Breuer | 435/34 |
| 4,042,462 | 8/1977 | Johnson et al. | 435/34 |
| 4,241,178 | 12/1980 | Esders et al. | 435/15 |
| 4,243,539 | 1/1981 | Farcasiu et al. | 568/729 |
| 4,245,041 | 1/1981 | Denney | 435/15 |
| 4,391,904 | 7/1983 | Litman et al. | 435/7 |
| 4,472,498 | 9/1984 | Masuda et al. | 435/7.1 |
| 4,576,913 | 3/1986 | Adachi et al. | 435/26 |
| 4,610,961 | 9/1986 | Guardino et al. | 435/34 |
| 4,629,697 | 12/1986 | Limbach et al. | 435/26 |
| 4,728,608 | 3/1988 | Roberts et al. | 435/34 |
| 4,791,057 | 12/1988 | Misaki et al. | 435/26 |
| 4,803,161 | 2/1989 | Babb et al. | 435/29 |
| 4,849,330 | 7/1989 | Humphries et al. | 436/904 |
| 4,853,186 | 8/1989 | Mura et al. | 436/903 |
| 4,857,271 | 8/1989 | Belly et al. | 436/903 |
| 4,898,813 | 2/1990 | Albarella et al. | 435/4 |
| 4,912,035 | 3/1990 | Belly et al. | 435/25 |
| 5,013,669 | 5/1991 | Peters et al. | 436/518 |
| 5,059,526 | 10/1991 | Arai et al. | 435/17 |

OTHER PUBLICATIONS

Equchi et al., Tetrazolium Salt Method Coupled with a Phenazinium Salt Gives Higher Rates for Dehydrogenase Reactions, (1985), vol. 63, No. 6, pp. 563–565, J. Fermentation Technology. Month not available. (Please print).

Lott et al., Stabilization of the Free–Radical Product of Phenazine Methosulphate in Bile and Formation of the Free–Radical Product in vitro by Reaction with Bilirubin, (1979), vol. 1, pp. 926–928, Biochemical Society Transactions. Month not available. (Please print).

Ghosh et al., Phenazine Ethosulfate as a Preferred Electron Acceptor to Phenazine Methosulfate in Dye–Linked Enzyme Assays, (1979), pp. 112–117, Analytical Biochemistry, 99. Month not available. (Please print).

Prince et al., The Thermodynamic Properties Of Some Commonly Used Oxidation–Reduction Mediators, Inhibitors And Dyes, As Determined By Polarography, (1981), pp. 132–148, Biochimica et Biophysica Acta, 635. Month not available. (Please print).

Halaka et al., Properties of 5–Methyphenazinium Methyl Sufate, issued of Feb. 10, 1982, pp. 1458–1462, Journal of Biological Chemistry. Month not available. (Please print).

Dawson et al., Artificial and Natural Substrates, 3rd Edition, 1986, pp. 356–357, Data for Biochemical Research. Month not available. (Please print).

*Primary Examiner*—Louise Leary
*Attorney, Agent, or Firm*—D. Michael Young

[57] ABSTRACT

A new reagent and methods for measuring the concentration of (or detecting the presence of) an analyte in a sample. The reagent includes a phenazine-containing compound and an enzyme. The phenazine-containing compound must be of sufficient type to form a semiquinoid (the color indicator) by reaction involving the enzyme, analyte, and phenazine-containing compound. Importantly, the phenazine-containing compound must be in sufficient amount to correlate the concentration of semiquinoid to the concentration of analyte in the sample or to detect the presence of the analyte in the sample. The reagent may further include a buffer and a surfactant. The reagent may be incorporated into a film and may be provided in kit form.

The methods for measuring the amount of (or detecting the presence of) an analyte in a sample importantly include spectrophotometric measurement (or detection) of the semiquinoid indicator at wavelengths greater than about 580 nanometers, which reduces interferences due to the presence of hemoglobin, bilirubin, and turbidity. Further, these assay methods importantly involve short incubation periods of less than about one minute for test samples measuring (or detecting) spectrophotometric absorbance (assays performed on solutions) and less than about 1.5 minutes for test samples measuring (or detecting) spectrophotometric reflectance or transmittance (assays performed on films).

32 Claims, No Drawings

REAGENT AND ASSAY METHODS INCLUDING A PHENAZINE-CONTAINING INDICATOR

This application is a continuation of Ser. No. 08/150751, filed on Nov. 12, 1993, now abandoned, which is a continuation-in-part of Ser. No. 07/762278, filed Sep. 19, 1991, now abandoned.

FIELD OF THE INVENTION

This invention relates to the colorimetric measurement of the amount of an analyte in a sample.

BACKGROUND OF THE INVENTION

In colorimetric assays for measuring the amount of an analyte in a sample, phenazine-containing compounds have been used as mediators (redox mediators) in oxidation-reduction reactions to facilitate the reduction of an indicator. In such assays, the color intensity of the reduced form of the indicator is correlated to the amount of analyte in the sample. The following reaction sequences are exemplary of these assays:

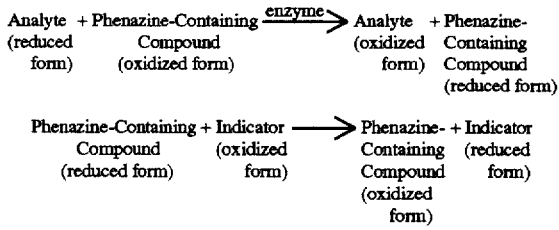

Phenazine-Containing Compound (oxidized form)=e.g., PMS (phenazine methosulfate)

Indicator (oxidized form)=e.g., tetrazolium salt, NAD (oxidized form of nicotinamide adenine dinucleotide)

Indicator (reduced form)=e.g., formazan, NADH (reduced form of nicotinamide adenine dinucleotide)

When used as redox mediators, phenazine-containing compounds function as non-enzymatic catalysts and their concentration in an assay is very low (significantly less than one millimolar).

SUMMARY OF THE INVENTION

The invention is a new reagent for measuring the concentration of (or detecting the presence of) an analyte that will react with an oxidase enzyme capable of reacting with oxygen to form hydrogen peroxide or with a dehydrogenase enzyme. The reagent includes the following: 1) a phenazine-containing compound that will react with the reduced form of the oxidase enzyme or the reduced form of nicotinamide adenine dinucleotide (NADH) and 2) the oxidized form of the oxidase enzyme or the oxidized form of the dehydrogenase enzyme (and the oxidized form of nicotinamide adenine dinucleotide (NAD)). Importantly, the phenazine-containing compound must be in sufficient amount to correlate the concentration of semiquinoid (the color indicator), formed by reduction of the phenazine-containing compound, to the concentration of analyte in the sample (or to detect the presence of the analyte in the sample).

The reagent may also include the following components: A buffer to provide a pH at which the oxidase enzyme or the dehydrogenase enzyme functions as a catalyst and a surfactant in sufficient amount to prevent precipitation of the semiquinoid in an aqueous solution.

A reagent kit for measuring the amount of an analyte in a sample may also be provided. In the reagent kit, a first reagent includes the phenazine-containing compound, and a second reagent includes the enzyme and the buffer.

The inventive reagent may be incorporated into a film, which at a minimum includes the phenazine-containing compound, enzyme, and a film forming agent, such as NATROSOL-250M, which is a micro-crystalline hydroxyethylcellulose, available from Aqualon Company (Little Falls Centre One, 2711 Centerville Road, P.O. Box 15417, Wilmington, Del. 19850-5417). The film may further include a buffer, a reagent stabilizer, and a surfactant.

Alternatively, the inventive reagent may impregnate a fabric mesh (such as a nylon mesh) or paper. The reagent may also be coated onto glass fibers.

The methods for measuring the amount of (or detecting the presence of) an analyte in a sample importantly include spectrophotometric measurement (or detection) of the semiquinoid indicator at wavelengths greater than about 580 nanometers, which reduces interferences due to the presence of hemoglobin, bilirubin, and turbidity. Further, these assay methods importantly involve short incubation periods of less than about 30 seconds for test samples measuring spectrophotometric absorbance (assays performed on solutions) and less than about 1.5 minutes for test samples measuring spectrophotometric reflectance or transmittance (assays performed on films).

DETAILED DESCRIPTION OF THE INVENTION

Traditionally, phenazine-containing compounds have been used in low concentration as redox mediators (electron carriers) in the assay of analytes. For example, a phenazine-containing compound typically acts as a redox mediator in a reaction involving an enzyme, an analyte, and a dye, such as a tetrazolium salt. In such a reaction, the phenazine-containing compound acts as a redox mediator in reducing the dye. The reduced dye is a color indicator, such as a formazan, which is used in measuring the amount of analyte in a sample.

However, if a phenazine-containing compound is supplied in high enough concentration relative to the amount of analyte being measured, it behaves as an indicator rather than merely as an electron carrier in the assay of an analyte.

When spectrophotometric measurements of a solution are performed, the present inventive reagent minimally includes a phenazine-containing compound and an enzyme, as described below.

Specifically, the enzyme must be an oxidase enzyme capable of reacting with oxygen to form hydrogen peroxide, such as glucose oxidase, or a dehydrogenase enzyme, such as glucose dehydrogenase. The phenazine-containing compound must be capable of reacting with the reduced form of the oxidase enzyme or, if a dehydrogenase enzyme is included in the reagent, with the reduce form of nicotinamide adenine dinucleotide (NADH). Examples of such compounds include phenazine ethosulfate, phenazine methosulfate, N-ethylmethoxyphenazine ethosulfate (available from Research Organics, Inc., Cleveland, Ohio), and 1-methoxyphenazine methosulfate (available from Research Organics, Inc.) However, N-ethylmethoxyphenazine ethosulfate and 1-methoxyphenazine methosulfate, as well as many other phenazine-containing compounds, are red colored, which creates a high blank reaction in an assay of an analyte. Therefore, phenazine ethosulfate and phenazine methosulfate are preferred phenazine-containing compounds because they are yellow colored and do not create a high blank reaction in the assay of an analyte.

Accordingly, the analyte that may be detected or measured in an assay utilizing the inventive reagent are those analytes that will react with an oxidase enzyme capable of reacting with oxygen to form hydrogen peroxide or with a dehydrogenase enzyme. Examples of such enzymes and the analytes that will react with those enzymes are listed below.

| Analytes | Oxidoreductase Enzymes Capable of Reacting with Oxygen to Form Hydrogen Peroxide |
|---|---|
| Glucose | Glucose oxidase |
| Cholesterol | Cholesterol Oxidase |
| Glycerol (Triglyceride test) | Glycerol 3-Phosphate Oxidase |
| L-Amino Acids | L-Amino Acid Oxidase |
| Acyl-CoA | Acyl-CoA Oxidase |
| Choline | Choline Oxidase |
| Putrescine (polyamine) | Putrescine Oxidase |
| Sarcosine | Sarcosine Oxidase |
| short chain alcohols | Alcohol Oxidase |
| L-Lactate | L-Lactate Oxidase |
| Pyruvate, Aspartate aminotransferase, Alanine aminotransferase analysis | Pyruvate Oxidase |
| Uric acid | Uricase |

| Analytes | Dehydrogenase Enzymes |
|---|---|
| Ethanol, acetaldehyde | Alcohol dehydrogenase |
| L-glycerol-3-phosphate (Triglyceride test) | Glycerol-3-phosphate dehydrogenase |
| glucose | Glucose dehydrogenase |
| glucose-6-phosphate (glucose test) | Glucose-6-phosphate dehydrogenase |
| Formaldehyde | Formaldehyde dehydrogenase |
| L-Glutamate | Glutamate dehydrogenase |
| D-3-Hydroxybutyrate (ketone bodies) | D-3-Hydroxybutyrate dehydrogenase |
| L-lactate | Lactate dehydrogenase |
| L-leucine | Leucine dehydrogenase |
| L-Malate | Malate dehydrogenase |
| assay of steroids | Hydroxysteroid dehydrogenase |

In addition to the specific phenazine-containing compounds listed above, other phenazine-containing compounds usable in the present inventive reagent could be easily screened. If the phenazine-containing compound readily reacts with a subcess of the reduced form of an oxidase enzyme described above, to form a colored compound (the semiquinoid), then the phenazine-containing compound is usable as a colored indicator in a reagent that includes the oxidase enzyme. If the phenazine-containing compound readily reacts with NADH to form a colored compound (the semiquinoid), then the phenazine-containing compound is usable as a colored indicator in a reagent that includes a dehydrogenase enzyme.

Color is generated in an assay performed with the present inventive reagents by the following generalized reaction schemes:

For assays of analytes that react with oxidase capable of reacting with oxygen to form hydrogen peroxide

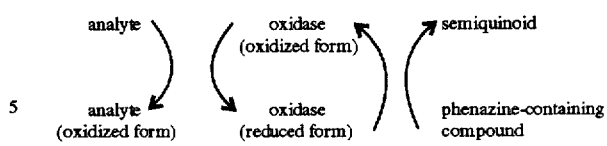

For assays of analytes that react with dehydrogenases

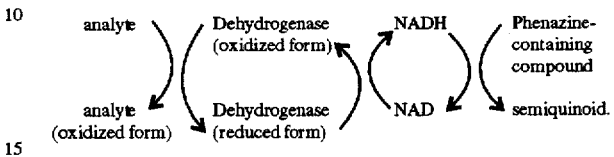

To correlate the concentration of semiquinoid to the concentration of glucose in a blood sample, the concentration of phenazine-containing compound in a reagent should be at least about four (4) millimolar (mM). For detection, rather than measurement, of glucose in a blood sample, the concentration of phenazine-containing compound in a reagent may be as low as about one (1) mM.

The minimum amount of phenazine-containing compound required in the reagent to measure or detect a particular analyte in a sample will depend upon the following factors:

1) the concentration of the analyte being measured;
2) the efficiency of the enzyme as a redox catalyst;
3) the numbers of transferred electrons;
4) if the enzyme is an oxidase, the efficiency of the oxidase's reaction with oxygen, which competes with phenazine-containing compound for reaction and the amount of oxygen available to react with the oxidase (that is, the more efficient the oxidase's reaction with oxygen and the more oxygen available to react with the oxidase, the more phenazine-containing compound needed in the reagent). The upper limit of the amount of phenazine-containing compound that may be provided in the reagent is limited by the solubility of the compound in the reagent.

The enzyme supplied to the reagent must be an oxidase enzyme capable of reacting with oxygen to form hydrogen peroxide or a dehydrogenase enzyme in sufficient amount to catalyze the reaction involving enzyme, analyte, and phenazine-containing compound. For example, if glucose is the analyte sought to be measured, the enzyme may be glucose oxidase. Likewise, cholesterol oxidase may be used in analyzing cholesterol and glycerol-3-phosphate oxidase may be used in analyzing glycerol-3-phosphate.

A buffer may sometimes be a required or a preferred additive to the reagent. The buffer must be of sufficient type and in sufficient amount to provide a pH at which the oxidase enzyme or the dehydrogenase enzyme functions as a catalyst in the reaction involving enzyme, analyte, and phenazine-containing compound. Examples of buffers that may be used in the reagent, depending upon the pH desired, include "Good" buffers, such as 2-(N-morpholino) ethanesulfonic acid, N-(2-acetamido)-2-iminodiacetic acid, piperazine-N,N/-bis (2-ethanesulfonic acid), N-(2-acetamido)-2-aminoethanesulfonic acid, N,N-bis (2-hydroxyethyl)-2-aminoethanesulfonic acid, N-tris (hydroxymethyl)methyl-2-aminoethanesulfonic acid, and N-2-hydroxyethylpiperazine-N/-2-ethanesulfonic acid. Maleic acid may also be used for glucose analysis.

A surfactant may also preferably be added to the reagent, particularly at higher phenazine-containing compound concentrations. The surfactant should be a nonionic surfactant in sufficient amount to prevent precipitation of the semiquinoid indicator. Examples of nonionic surfactants include polyoxyethylene ethers, polyoxyethylene sorbitans, and TRITON surfactants (available from Sigma Chemical Company).

Examples of anionic surfactants include sulfonate surfactants sold under the mark DOWFAX, available from Dow Corning Corp., and sulfonate surfactants sold under the mark MARLON, available from Chemische Werke Huls AG.

Specific reagents for the analysis of specific analytes may be formulated as follows:

Glucose Reagent

Step 1—A buffer stock solution was prepared by dissolving about 3.9 grams (g) of 2-(N-morpholino) ethanesulfonic acid in about 100 milliliters (ml) of distilled water. (The concentration of 2-(N-morpholino) ethanesulfonic acid in the buffer stock solution was about 200 mM.) The pH of the resulting solution was adjusted to about 5.6 with sodium hydroxide.

Step 2—An enzyme-containing solution was prepared by dissolving about 6 kilounits (ku) of glucose oxidase (*Aspergillus niger*) in about 8 ml of the buffer stock solution.

Step 3—A phenazine-containing compound solution was prepared by dissolving about 3.3 g of phenazine ethosulfate in about 25 ml of distilled water. (This solution was about 400 mM in phenazine ethosulfate.)

A single glucose reagent may be prepared by combining the enzyme-containing solution with the phenazine-containing compound solution in a ratio of about 9:1 (volume:volume). Alternatively, a reagent kit may be provided, wherein the enzyme-containing solution and the phenazine-containing compound solution are each kept in separate vials (and may be lyophilized). When using the reagent kit, the enzyme-containing solution and the phenazine-containing compound solution should be combined in the above stated ratio (about 9:1) (volume:volume) to perform a glucose assay. (Lyophilized vials may also be reconstituted with water and combined in the above-stated ratio.)

Cholesterol Reagent

Step 1—A buffer stock solution may be prepared by dissolving about 6.3 g of 3-(N-morpholino) propanesulfonic acid in about 100 ml of distilled water. (The concentration of 3-(N-morpholino) propanesulfonic acid in the buffer stock solution will be about 300 mM.) The pH of the buffer stock solution may be adjusted to about 7.2 by the addition of 1 Normal (N) sodium hydroxide.

Step 2—About 2.2 ku of cholesterol oxidase (from *Nocardia erythropolis*) and about 104 milligrams (mg) of phenazine ethosulfate may be dissolved in 5.2 ml of the buffer stock solution. To the resulting solution, TRITON X-100 (a nonionic surfactant, available from Sigma Chemical Company) may be added in an amount which makes the resulting solution (the cholesterol reagent) one percent (volume:volume) TRITON X-100.

The cholesterol reagent may be provided as a single reagent or as a reagent kit. In a reagent kit, phenazine ethosulfate (preferably in lyophilized form) is provided in one container, and in a separate container the other reagent ingredients (preferably lyophilized) are provided.

Glycerol-3-Phosphate Reagent

Step 1—A buffer stock solution was prepared by dissolving about 3.6 g of N-2-hydroxyethylpiperazine-N/-2-ethanesulfonic acid in about 100 ml of distilled water. The pH of the resulting solution was adjusted to about 7.6 by the addition of 1N sodium hydroxide.

Step 2—An enzyme-containing solution was prepared by dissolving about 8 ku of glycerol-3-phosphate oxidase in about 8 ml of buffer stock solution.

Step 3—A phenazine-containing compound solution was prepared by dissolving about 3.3 g of phenazine ethosulfate in about 25 ml of distilled water. (The resulting concentration of phenazine ethosulfate was about 400 mM.)

A single glycerol-3-phosphate reagent may be obtained by combining the enzyme-containing solution with the phenazine-containing compound solution at a ratio of about 9:1 (volume:volume). A glycerol-3-phosphate reagent kit may also be provided by keeping the enzyme-containing solution and the phenazine-containing compound solution separate. (Each of these solutions is preferably lyophilized.) When the kit is used for an assay of glycerol-3-phosphate, the enzyme-containing reagent and the phenazine-containing compound reagent should be provided in the same proportions as specified above for the single glycerol-3-phosphate reagent. (These proportions also apply to kit reagents that are lyophilized and subsequently reconstituted by the addition of water.)

The above stated reagents are liquid reagents (or are liquid after lyophilized reagent is reconstituted with water). These reagents may also be incorporated into films. When incorporated into a film, the reagent minimally includes a phenazine-containing compound, an enzyme, and a film forming agent, such as a microcrystalline hydroxyethylcellulose.

As stated above for liquid and lyophilized reagents, in a film the phenazine-containing compound must be reactable with the reduced form of the oxidase enzyme or with NADH and must be in sufficient amount to detect the semiquinoid (thereby detecting the presence of the analyte) or to correlate the concentration of semiquinoid to the concentration of analyte in the sample being analyzed. Accordingly, the amount of phenazine-containing compound incorporated into the film for glucose analysis of a blood sample should be at least about 18 micromoles (μ mol) per g of dry film (assuming 100% dry or 100% solids in the film) for correlating the concentration of semiquinoid to the concentration of glucose in the sample being analyzed and at least about 11 μ mol per g of dry film to detect the presence of the glucose in the sample. The enzyme must also be in sufficient amount to catalyze the reaction involving enzyme, glucose, and phenazine-containing compound.

A buffer may also be incorporated into the film. The types of buffers that may be used and the requirements of those buffers are the same as those stated above for liquid and lyophilized reagents. (When films are used to perform assays, spectrophotometric reflectance or transmittance measurements are made rather than absorbance measurements.)

A reagent incorporated into a film may also include a nonionic or anionic surfactant. The surfactant must be in sufficient amount to wet the surface of the film upon addition of the sample being analyzed. Particularly preferred surfactants for films are anionic sulfonic acid surfactants, such as those surfactants sold under the marks MARLON and DOWFAX.

A specific example of a film that may be used for glucose analysis is as follows:

Glucose Film

| Film Component | Amount per kilogram of film (wet weight) |
| --- | --- |
| Malic Acid | 150 mM |
| Nickel Sulfate | 50 mM |
| Manganese Sulfate | 50 mM |
| *CELABRITE | 22% (weight:weight) |
| NATROSOL-250M | 0.75% (weight:weight) |
| Dextran Sulfate (molecular weight = 5000 g/mol) | 2% (weight:weight) |
| Glucose Oxidase (from Aspergillus Niger, available from Biozyme Laboratories Limited) | 1500 units/g wet film |
| ᵇPROPIOFAN 70D | 7% (weight:weight) |
| ᶜTWEEN 20 | 0.5% (weight:weight) |
| Phenazine Ethosulfate | 60 mM |
| Water | |

ᵃA diatomaceous earth, available from Eagle-Picher Industries, Inc., Cincinnati, Ohio.
ᵇAn aqueous vinyl propionate copolymer dispersion of large particle size, available from BASF Corporation. This composition contains a protective colloid.
ᶜPolyoxyethylenesorbitan monolaurate, available from Sigma Chemical Company.

This film may be coated onto 250 micrometer CRONAR plastic (a plastic with a gel backing available from DuPont). The wet coating may be dried at about 50° C. for 20 minutes to remove more than 90% of the water in the wet film.

The present inventive reagent may be advantageously incorporated into methods for measuring the amount of an analyte in a sample. The general method for measuring the amount of (or alternatively detecting the presence of) an analyte in a sample includes the following steps:

Step 1—forming a test sample by combining the sample containing the analyte with a single liquid reagent or a film (described above);

Step 2—incubating the test samples;

Step 3—spectrophotometrically measuring absorbance of the incubated test sample at a wavelength from about 520 nanometers (nm) to about 740 nm; and Step 4—correlating the measured absorbance of the incubated test sample to the amount (or to the presence) of analyte in the sample.

Importantly, the amount (or presence) of indicator (semiquinoid) may be spectrophotometrically measured (or detected) at wavelengths from about 580 to about 740 nm. Spectrophotometric measurement at these longer wavelengths decreases interference due to hemoglobin, bilirubin, and turbidity, which may be present in the sample being analyzed. Although spectrophotometric measurements may be made at wavelengths from about 520 to about 740 nm, spectrophotometric measurements are more preferably made at wavelengths from about 590 to about 710 nm and most preferably from about 620 to about 670 nm.

Another advantage of these methods for measuring an analyte in a sample is that the test sample incubation periods are much shorter than the test sample incubation periods of more traditional colorimetric assay methods. When a liquid reagent is used to measure the spectrophotometric absorbance of a solution, the incubation period may range from about 10 seconds to about 1 minute and will usually range from about 10 to about 40 seconds. When a film is used in the spectrophotometric measurements of reflectance or transmittance, the incubation period may range from about 20 seconds to about 1.5 minutes and will usually range from about 20 to about 60 seconds.

The present methods may be illustrated by the following examples:

EXAMPLE 1

Glucose Assay

Aqueous (distilled water) glucose stock solutions at concentrations of 189, 472.5, 787.5, and 1,417.5 mg per deciliter (dl), respectively, were prepared. An assay was conducted by separately combining 50 microliters (µl) of each glucose stock solution with 1 ml of the single specifically formulated liquid glucose reagent described above, thereby forming a test sample. Each test sample was incubated for about 15 seconds at ambient temperature. Spectrophotometric absorbance of each incubated test sample was then measured at 646 nm. There was direct correlation between the spectrophotometric absorbance of the test sample and the amount of glucose in the sample (stock solution) being analyzed.

EXAMPLE 2

Cholesterol Assay

PRECISET cholesterol standards (available from Boehringer Mannheim Corporation) may be used. Cholesterol standards of 0, 50, 100, 150, 200, 300, and 400 mg cholesterol per dl of standard, respectively, may be prepared. Assays of each cholesterol standard may be performed by combining 500 µl of cholesterol standard with 500 µl of the single specifically formulated liquid cholesterol reagent (described above), thereby forming a test sample. The test may be incubated for about 15 seconds at ambient temperature. Spectrophotometric absorbance of the test sample may then be measured at 602 nm. The intensity of spectrophotometric absorbance may be directly correlated to the amount of cholesterol in the cholesterol standard being analyzed.

EXAMPLE 3

Glycerol-3-Phosphate Assay

Aqueous (distilled water) glycerol-3-phosphate standards of 22.1, 44.2, and 66.3 mM were prepared. Test samples were prepared by separately adding 50 µl of each glycerol-3-phosphate stock solution to 1 ml of the specifically formulated glycerol-3-phosphate liquid reagent described above. Each test sample was incubated for about 15 seconds at ambient temperature. The spectrophotometric absorbance of each incubated test sample was measured at 602 nm. The intensity of spectrophotometric absorbance directly correlated to the amount of glycerol-3-phosphate in each glycerol-3-phosphate standard.

When an assay method employs a reagent kit (as described above), the first and second reagent of the kit may be combined (to form a single liquid reagent, as described above) prior to the addition of the sample to be analyzed. Alternatively, an intermediate sample may be formed by combining the sample containing the analyte with the first reagent of the kit. (The first reagent includes the phenazine-containing compound.) A test sample is then formed by combining the intermediate sample with the second reagent of the kit. (The second reagent of the kit includes the enzyme and buffer.) The test sample is then incubated (as described above), and the incubated test sample is spectrophotometrically measured (as described above). In an assay that utilizes an oxidase enzyme capable of reacting with oxygen to form hydrogen peroxide, the incubation period should be triggered by addition of the enzyme or the analyte sought to be measured rather than the phenazine-containing compound. (If the analyte sought to be measured and the oxidase enzyme are combined prior to the addition of the phenazine-containing compound, an unwanted reaction involving enzyme, analyte, and oxygen (forming hydrogen peroxide) may occur.)

When a film is used instead of a liquid reagent, the test sample is formed by combining a liquid sample containing the analyte with the film. (See Step 1 of the general method.) The test sample is then incubated from about 20 to about 60 seconds at ambient temperature. (See Step 2 of the general method.) Reflectance or transmittance of the incubated test sample is then measured (or detected) at the wavelengths specified above. (See Step 3 of the general method.) The intensity of reflectance or transmittance of the incubated test sample is inversely proportional to the amount of analyte in the sample being analyzed. (See Step 4 of the general method.)

The present invention has been disclosed in the above teachings with sufficient clarity and conciseness to enable one skilled in the art to make and use the invention, to know the best mode for carrying out the invention, and to distinguish it from other inventions and from what is old. Many variations and obvious adaptations will readily come to mind, and these are intended to be contained within the scope of the invention as claimed below.

We claim:

1. A reagent for detecting the presence of an analyte that will react with an oxidase enzyme capable of reacting with oxygen to form hydrogen peroxide, consisting essentially of:
   a catalytic amount of the oxidized form of the oxidase enzyme; and
   a phenazine-containing compound that will react with the reduced form of the oxidase enzyme, the phenazine-containing compound being in sufficient amount to form a detectable, colored semiquinoid upon reaction of the phenazine-containing compound with the reduced form of the oxidase enzyme, thereby indicating the presence of the analyte,
   whereby the phenazine-containing compound functions as an indicator compound and not as a redox mediator.

2. The reagent of claim 1, wherein the phenazine-containing compound is phenazine methosulfate, phenazine ethosulfate, N-ethylmethoxyphenazine ethosulfate, or 1-methoxyphenazine methosulfate.

3. The reagent of claim 2, further consisting essentially of:
   a sufficient amount of water to form a solution;
   a sufficient amount of a buffer to provide a pH at which the oxidase enzyme functions as a catalyst; and
   a sufficient amount of a nonionic or an anionic surfactant to prevent precipitation of the semiquinoid.

4. The reagent of claim 2, further consisting essentially of:
   a film-forming agent in sufficient amount to form a film;
   a sufficient amount of a buffer to provide a pH at which the oxidase enzyme will function as a catalyst when the reagent is hydrated; and
   a sufficient amount of a nonionic or an anionic surfactant to aid in hydrating the reagent when a water-containing liquid sample is added to the reagent.

5. The reagent of claim 1, further consisting essentially of:
   a sufficient amount of water to form a solution, and wherein the analyte is glucose and the concentration of the phenazine-containing compound is at least about one millimolar.

6. The reagent of claim 1, further consisting essentially of:
   a film-forming agent in sufficient amount to form a film, and wherein the analyte is glucose and the amount of phenazine-containing compound is at least about 11 micromoles per gram of reagent.

7. A reagent for detecting the presence of an analyte that will react with the oxidized form of a dehydrogenase enzyme, thereby forming the reduced form of the dehydrogenase enzyme, consisting essentially of:
   a catalytic amount of the oxidized form of the dehydrogenase enzyme;
   a catalytic amount of the oxidized form of nicotinamide adenine dinucleotide; and
   a phenazine-containing compound that will react with the reduced form of nicotinamide adenine dinucleotide, the phenazine-containing compound being in sufficient amount to form a detectable, colored semiquinoid upon reaction of the phenazine-containing compound with the reduced form of the nicotinamide adenine dinucleotide, thereby indicating the presence of the analyte,
   whereby the phenazine-containing compound functions as an indicator compound and not as a redox mediator.

8. The reagent of claim 7, wherein the phenazine-containing compound is phenazine methosulfate, phenazine ethosulfate, N-ethylmethoxyphenazine ethosulfate, or 1-methoxyphenazine methosulfate.

9. The reagent of claim 8, further consisting essentially of:
   a sufficient amount of water to form a solution;
   a sufficient amount of a buffer to provide a pH at which the dehydrogenase enzyme functions as a catalyst; and
   a sufficient amount of a nonionic or an anionic surfactant to prevent precipitation of the semiquinoid.

10. The reagent of claim 8, further consisting essentially of:
    a film-forming agent in sufficient amount to form a film;
    a sufficient amount of a buffer to provide a pH at which the dehydrogenase enzyme will function as a catalyst when the reagent is hydrated; and
    a sufficient amount of a nonionic or an anionic surfactant to aid in hydrating the reagent when a water-containing liquid sample is added to the reagent.

11. The reagent of claim 7, further consisting essentially of:
    a sufficient amount of water to form a solution, and wherein the analyte is glucose and the concentration of the phenazine-containing compound is at least about 1 millimolar.

12. The reagent of claim 7, further consisting essentially of:
    a film-forming agent in sufficient amount to form a film, and wherein the analyte is glucose and the amount of phenazine-containing compound is at least about 11 micromoles per gram of reagent.

13. A reagent for measuring the amount of an analyte that will react with an oxidase enzyme capable of reacting with oxygen to form hydrogen peroxide, consisting essentially of:
    a catalytic amount of the oxidized form of the oxidase enzyme; and
    a phenazine-containing compound that will react with the reduced form of the oxidase enzyme, the phenazine-containing compound being in sufficient amount to form a measurable, colored semiquinoid upon reaction of the phenazine-containing compound with the reduced form of the oxidase enzyme, thereby indicating the amount of the analyte, whereby the phenazine-containing compound functions as an indicator compound and not as a redox mediator.

14. The reagent claim 13, wherein the phenazine-containing compound is phenazine methosulfate, phenazine ethosulfate, N-ethylmethoxyphenazine ethosulfate, or 1-methoxyphenazine methosulfate.

15. The reagent of claim 14, further consisting essentially of:

a sufficient amount of water to form a solution.

16. The reagent of claim 15, further consisting essentially of:

a sufficient amount of a buffer to provide a pH at which the oxidase enzyme functions as a catalyst.

17. The reagent of claim 16, further consisting essentially of:

a sufficient amount of a nonionic or an anionic surfactant to prevent precipitation of the semiquinoid.

18. The reagent of claim 14, further consisting essentially of:

a film-forming agent in sufficient amount to form a film.

19. The reagent of claim 18, further consisting essentially of:

a sufficient amount of a buffer to provide a pH at which the oxidase enzyme will function as a catalyst when the reagent is hydrated.

20. The reagent of claim 19, further consisting essentially of:

a sufficient amount of a nonionic or an anionic surfactant to aid in hydrating the reagent when a water-containing liquid sample is added to the reagent.

21. The reagent of claim 13, further consisting essentially of:

a sufficient amount of water to form a solution, and wherein the analyte is glucose and the concentration of the phenazine-containing compound is at least about 4 millimolar.

22. The reagent of claim 13, further consisting essentially of:

a film-forming agent in sufficient amount to form a film, and wherein the analyte is glucose and the amount of phenazine-containing compound is at least about 18 micromoles per gram of reagent.

23. A reagent for measuring the amount of an analyte that will react with the oxidized form of a dehydrogenase enzyme, thereby forming the reduced form oft he dehydrogenase enzyme, consisting essentially of:

a catalytic amount of the oxidized form of the dehydrogenase enzyme;

a catalytic amount of the oxidized form of nicotinamide adenine dinucleotide; and a phenazine-containing compound that will react with the reduced form of nicotinamide adenine dinucleotide, the phenazine-containing compound being in sufficient amount to form a measurable, colored semiquinoid upon reaction of the phenazine-containing compound with the reduced form of nicotinamide adenine dinucleotide, thereby indicating the amount of the analyte, whereby the phenazine-containing compound functions as an indicator compound and not as a redox mediator.

24. The reagent of claim 23, wherein the phenazine-containing compound is phenazine methosulfate, phenazine ethosulfate, N-ethylmethoxyphenazine ethosulfate, or 1-methoxyphenazine methosulfate.

25. The reagent of claim 24, further consisting essentially of:

a sufficient amount of water to form a solution.

26. The reagent of claim 25, further consisting essentially of:

a sufficient amount of a buffer to provide a pH at which the dehydrogenase enzyme functions as a catalyst.

27. The reagent of claim 26, further consisting essentially of:

a sufficient amount of a nonionic or an anionic surfactant to prevent precipitation of the semiquinoid.

28. The reagent of claim 24, further consisting essentially of:

a film forming agent in sufficient amount to form a film.

29. The reagent claim 28, further consisting essentially of:

a sufficient amount of a buffer to provide a pH at which the dehydrogenase enzyme will function as a catalyst when the reagent of is hydrated.

30. The reagent of claim 29, further consisting essentially of:

a sufficient amount of a nonionic or an anionic surfactant to aid in hydrating the reagent when a water-containing liquid sample is added to the reagent.

31. The reagent of claim 23, further consisting essentially of:

a sufficient amount of water to form a solution, and wherein the analyte is glucose and the concentration of the phenazine-containing compound is at least about 4 millimolar.

32. The reagent of claim 23, further consisting essentially of:

a film-forming agent in sufficient amount to form a film, and wherein the analyte is glucose and the amount of phenazine-containing compound is at least about 18 micromoles per gram of reagent.

* * * * *